(12) United States Patent
Mount et al.

(10) Patent No.: US 6,896,892 B2
(45) Date of Patent: May 24, 2005

(54) INSECTICIDE-IMPREGNATED FABRIC AND METHOD OF PRODUCTION

(75) Inventors: Dwight L. Mount, Duluth, GA (US); Michael D. Green, Winder, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/168,666

(22) PCT Filed: Feb. 12, 2001

(86) PCT No.: PCT/US01/40092

§ 371 (c)(1), (2), (4) Date: Jun. 24, 2002

(87) PCT Pub. No.: WO01/58261

PCT Pub. Date: Aug. 16, 2001

(65) Prior Publication Data

US 2003/0003126 A1 Jan. 2, 2003

Related U.S. Application Data

(60) Provisional application No. 60/181,770, filed on Feb. 11, 2000.

(51) Int. Cl.⁷ .............................................. A01N 25/34
(52) U.S. Cl. ..................................................... 424/411
(58) Field of Search ................................ 424/411, 405

(56) References Cited

U.S. PATENT DOCUMENTS

| 3,846,551 | A | | 11/1974 | Mifune et al. | |
|---|---|---|---|---|---|
| 4,722,815 | A | * | 2/1988 | Shibanai | .................... 264/117 |
| 5,089,298 | A | | 2/1992 | McNally et al. | |
| 5,139,687 | A | | 8/1992 | Borgher, Sr. et al. | ........ 252/8.6 |
| 5,252,387 | A | | 10/1993 | Samson et al. | ................ 442/67 |
| 5,503,918 | A | | 4/1996 | Samson et al. | |
| 5,554,649 | A | | 9/1996 | Ishiwatari et al. | .......... 428/248 |
| 5,631,072 | A | | 5/1997 | Samson et al. | |

FOREIGN PATENT DOCUMENTS

| JP | 63 130502 | | 6/1988 |
|---|---|---|---|
| JP | 01225644 | * | 8/1989 |
| JP | 2 160537 | | 6/1990 |
| JP | 1116756 | * | 4/1999 |

OTHER PUBLICATIONS

Curtis et al., "Comparison of different insecticides and fabrics for anti–mosquito bednets and curtains," *Medical and Veterinary Entomology Blackwell Scientific Public.*, Oxford, GB, vol. 10, No. 1, pp. 1–11 (1996).

Lindsay et al., "Preliminary studies on the insecticidal activity and wash–fastness of twelve pyrethroid treatments impregnated into bednetting assayed against mosquitoes," *Pesticide Science*, vol. 32, No. 4, pp. 397–411 (1991).

* cited by examiner

*Primary Examiner*—Alton Pryor
(74) *Attorney, Agent, or Firm*—Needle & Rosenberg, P.C.

(57) ABSTRACT

An insecticide-impregnated fabric that remains sufficiently effective at killing and repelling disease vector insects after repeated washings with detergent and water is described. The fabric is impregnated with an insecticide composition containing an insecticide, a cyclodextrin, and a binding agent. The resulting fabric is useful for providing personal protection against disease-carrying insect vectors, particularly when assembled as a bednet in regions of the world where malaria is prevalent, and will remain effective for a longer period of time before re-impregnation is necessary.

19 Claims, 14 Drawing Sheets

Figure 7

INSECTICIDE-IMPREGNATED FABRIC AND METHOD OF PRODUCTION

The present application is a 35 U.S.C. §371 national phase application from, and claims priority to, international application PCT/US01/40092, filed Feb. 12, 2001 (published under PCT Article 21(2) in English), which claims priority to U.S. provisional patent application Ser. No. 60/181,770, filed Feb. 11, 2000, which applications are incorporated herein in their entirety by reference.

CROSS REFERENCE TO RELATED APPLICATIONS

This application claims the benefit of U.S. Provisional Application 60/181,770, filed Feb. 11, 2000.

This invention was made at the Centers for Disease Control and Prevention. Therefore, the United States Government has certain rights in this invention.

FIELD OF THE INVENTION

The present invention relates to a fabric or net that has been impregnated or coated with an insecticide and methods of producing the fabric.

BACKGROUND OF THE INVENTION

Malaria is a major cause of child mortality in much of Africa. The mosquito parasite, *Plasmodium falciparum*, accounts for greater than 25% of childhood mortality outside the neonatal period. In parts of Africa, malaria has been ranked first by the World Bank in terms of disability-adjusted life-years lost. Drug and insecticide resistance, as well as insufficiently developed and financed health services, have hampered efforts over the past twenty years to improve the situation. As a result, the malaria burden has remained largely unchanged.

Mortality in young children due to mosquito-borne malaria poses a significant world health problem. Insecticide-treated nets and fabrics have been developed since the 1980s as a promising tool for the prevention of malaria in endemic countries. Potent and safe synthetic pyrethroids, such as, permethrin, deltamethrin, lambda-cyhalothrin, alphamethrin, and cyfluthrin, are presently used to treat bednets and curtains by simply dipping the fabric into a solution containing the insecticide and allowing the solution to dry on the fabric. Provided that the nets or fabrics are not washed more than once to twice, insecticidal activity is retained for up to twelve months.

Many studies documenting the efficacy of these nets or fabrics to reduce the number of outbreaks of malaria in endemic areas have been conducted in several countries. Recently, the World Health Organization (WHO), along with twenty other donor agencies, supported four large-scale trials in Africa to document the impact of treated bednets on child survival. The results indicated that the reduction in child mortality with the use of treated nets ranged from 16–33%. Treated nets, in combination with the use of insect repellents, have been suggested as a primary means of protection for high-risk travelers. Although little evidence is presently available to document the efficacy of treated nets or fabrics for travelers at high risk, the available evidence is so compelling that specific recommendations are often issued to all travelers exposed to situations that place them at risk for malaria.

Bednets treated with insecticides have been effective in the control of malaria in many countries. The treated bednets are an effective method of vector control in areas endemic for malaria and greatly enhance personal protection. Although there is some concern that the placement of the insecticide-treated fabric in close proximity to the skin, eyes, or mouth of the person being protected may be harmful, existing toxicology data on pyrethroids indicates that unlike other types of insecticides, these chemicals have been shown to be very safe.

The application of a residual insecticide to fabrics as a means of personal protection against vector-borne diseases has been attempted for some time. During World War II, the impregnation of bednets and combat fatigues by the Soviet, German, and U.S. armies was first tried. In the late 1970s pyrethroids were used for this purpose; their high insecticidal activity combined with low mammalian toxicity made them ideal for treating fabrics. A scientific panel convened in 1983 by WHO reviewed the first laboratory evidence and recommended the initiation of field trials to assess the potential of this technology for disease control.

Unfortunately, currently employed techniques for treating fabrics with insecticides are unable to maintain an effective level of active ingredient at the surface of the net or fabric to kill or repel mosquitoes, especially after repeated washings. In addition, currently available methods for applying insecticides to fabrics are expensive, which make their use impractical for underdeveloped countries. Furthermore, the available techniques utilize emulsions that vary greatly between manufacturers and do not provide consistent and effective results.

Therefore, what is needed is a wash durable insecticide treated net or fabric wherein the active ingredient is easily incorporated into the fabric and is prevented from being washed off, thereby maintaining the insecticide at the fabric surface to permit interaction with target arthropods for a prolonged period of time, even after repeated washings.

SUMMARY OF THE INVENTION

An insecticide-impregnated fabric and all insecticide composition for impregnating fabric are provided. The impregnated fabric maintains a sufficient amount of insecticide on the fabric surface to kill or repel insects, particularly mosquitoes, even after repeated washings. The fabric can be made into a net, clothing, and the like, for protection against insect-transmitted diseases such as malaria. Methods for producing the insecticide-impregnated fabric are also provided. In addition, an insecticide composition for treating fabrics is provided.

The insecticide solution contains a water-soluble cyclodextrin, a polymeric binding agent, and an insecticide. The preferred binding agent is polyvinyl acetate (PVA). The preferred insecticide is a pyrethroid. The cyclodextrin and insecticide in the insecticide solution bind together to form an inclusion complex, wherein the insecticide acts as a "guest molecule" nestling in the center of the hydrophobic interior of the water-soluble cyclodextrin. The fabric is impregnated by immersing the fabric in the insecticide solution and allowing the wetted fabric to dry. The inclusion complex binds to the fabric and allows the insecticide to remain attached to the fabric, even after several washes with a detergent and rinses, thereby prolonging the insecticidal effectiveness of the fabric.

Treatment of fabric with the insecticide composition described herein reduces the rate at which the insecticide is removed from the treated net during washings. Fabrics treated with the insecticide solution provide higher insect mortality than fabrics treated using solutions that lack the combination of a water-soluble cyclodextrin and a polymeric binding agent. Increased insecticidal effectiveness and wash-durability correlate strongly with the concentrations of cyclodextrin and binding agent in the solution used to treat the fabric.

The method provided herein is a simple process that combines the use of polymer water-compatible emulsions and a water-soluble cyclodextrin to attach insecticide to bed nets and other fabrics. Use of the method described herein results in a product that is superior over presently available bednets and provides a more durable and effective insecticide barrier at the surface of the net or fabric. The use of the treated nets and fabrics provided herein results in more effective nuisance and/or vector arthropod control, which is associated with a reduction in disease transmission.

The insecticide-impregnated fabric can be used in the manufacture of various end-user items such as, but not limited to netting, clothing, bedding, curtains and tents. Alternatively, fabric and existing fabric products can be treated and retreated with the insecticide composition using the method described herein. The fabric-impregnating method, using the insecticide composition, results in a product that is superior in performance, simpler to use, and lower in cost than currently available insecticide-impregnating or coating methods. Furthermore, the materials used in the method are less hazardous and more environmentally acceptable than those currently available.

It is therefore an object of the present invention to provide an insecticide-impregnated fabric in which the insecticide has extended effectiveness after multiple washings of the impregnated fabric with a detergent.

It is a further object of the present invention to provide a simple, inexpensive method for impregnating an insecticide into a fabric, particularly permethrin formulations.

It is a further object of the present invention to provide an inexpensive insecticide composition to be used to impregnate a fabric wherein the composition can be easily and quickly applied to the fabric.

These and other objects, features and advantages of the present invention will become apparent after a review of the following detailed description of the disclosed embodiment and the appended claims.

BRIEF DESCRIPTION OF THE DRAWINGS

FIG. 7 is a graph showing the effect of wash/rinse cycles on mosquito knock-down after exposure of *A. gambiae* (AB) to polypropylene bednet samples coated with permethrin (250 mg/m$^2$, diamonds; 500 mg/m$^2$, squares; 1000 mg/m$^2$, triangles) in combination with PVA (300, 600, and 1200 mg/m$^2$, respectively) and cyclodextrin (1250, 2500, and 5000 mg/m$^2$, respectively).

DETAILED DESCRIPTION OF THE INVENTION

Figure 1:
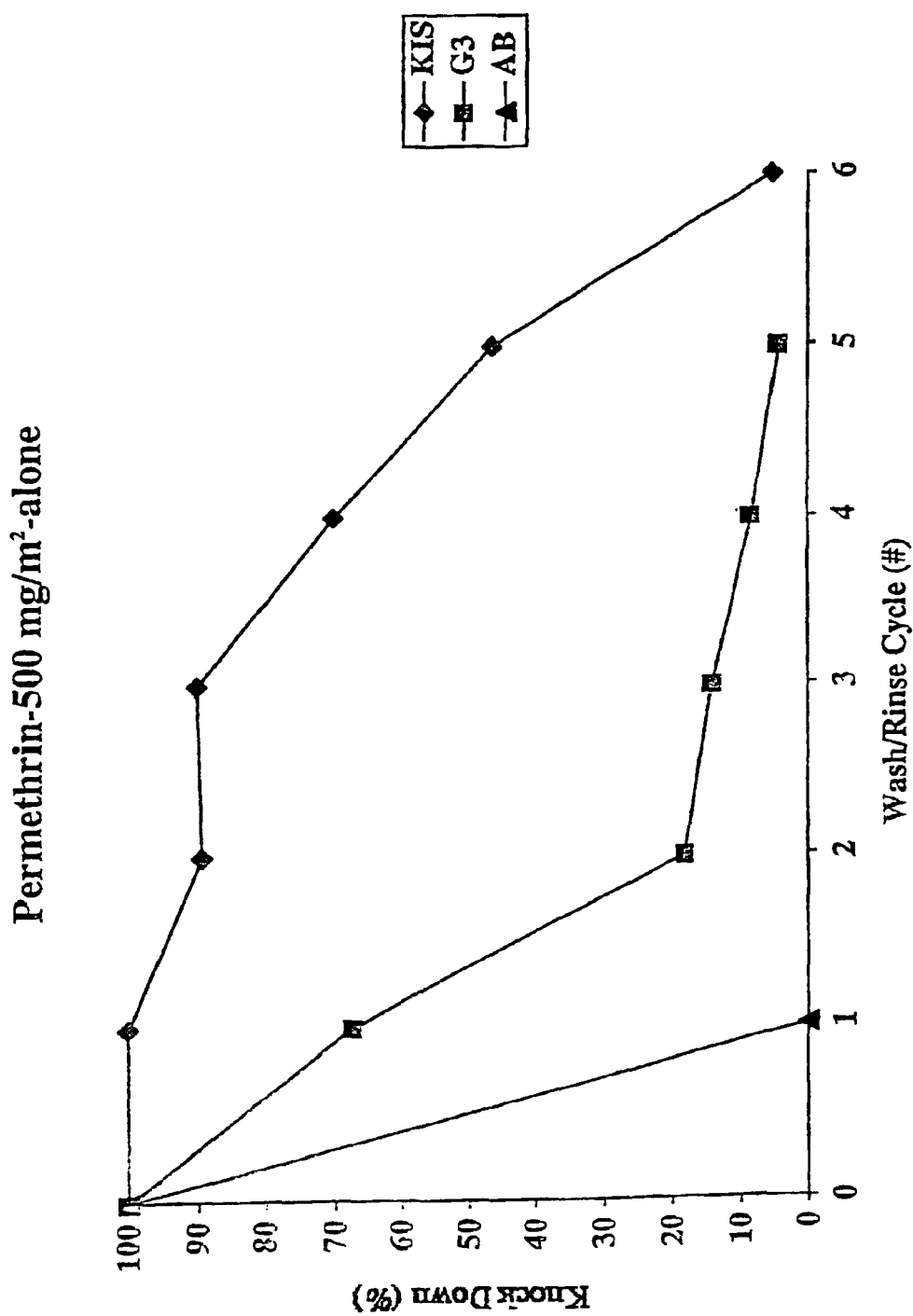
FIG. 1 is a graph showing the effect of wash/rinse cycles on mosquito knock-down after exposure of three strains of *A. gambiae* (KIS, diamonds; G3, squares; AB, triangles) to polypropylene bednet samples coated with permethrin alone (500 mg/m$^2$).

An insecticide-impregnated fabric is provided herein. The impregnated fabric maintains a sufficient amount of insecticide on the fabric surface to kill or repel disease vector arthropods or insects, particularly mosquitoes, even after repeated washings with detergent and water. The fabric can be sewn or otherwise constructed into a bednet, tent, clothing or outerwear as well as an outer covering for furniture and the like, for protection against insect-transmitted diseases such as malaria.

An insecticide composition for treating fabrics and methods for producing insecticide-impregnated fabrics are also provided. The insecticide composition is a solution, emulsion or suspension containing a water-soluble cyclodextrin, a commercial polymer emulsion as a binding agent, and an insecticide in an emulsifiable concentrate. In accordance with the production method, the fabric is impregnated by immersion in the insecticide solution and allowed to dry. The preferred binding agent is polyvinyl acetate (PVA). The preferred insecticide is a pyrethroid. The preferred cyclodextrin is a hydroxypropyl cyclodextrin. The cyclodextrin and insecticide in the insecticide solution bind to each other to form an inclusion complex, wherein the insecticide acts as a "guest molecule" nestling in the center of the hydrophobic interior of the water soluble cyclodextrin. The inclusion complex binds to the fabric and allows the insecticide to remain attached to the fabric, even after repeated washes with a detergent, thereby prolonging the insecticidal effectiveness of the fabric.

Insecticide

The insecticide used in the insecticide solution/emulsion is preferably (for reasons of human safety) a member of the pyrethroid family of insecticides, which includes, but is not limited to, permethrin, deltamethrin, cyfluthrin, alpha-cypermethrin, etofenprox and lambda-cyhalothrin. This group of insecticides is particularly effective against malaria-bearing mosquitoes and is relatively safe and non-toxic to humans. This latter characteristic makes these insecticides especially desirable for use in fabrics or garments which are to be worn close to or adjacent to the skin or body.

Permethrin is a third generation synthetic pyrethroid that has been approved for use by the Environmental Protection Agency (EPA) and the WHO. It is the constituent of many household and agricultural insecticidal formulations and has also been used to impregnate army battle-dress uniforms in the field. Currently available formulations and methods of application have allowed only limited use of permethrin due to the fact that it washes out of treated fabrics within three to four washings. The formulation and method of application described herein overcome this severe disadvantage.

Deltamethrin is also a synthetic pyrethroid-based insecticide. It is a unique insecticide among synthetic pyrethroids in that it has a much longer duration of activity, and its insecticidal activity is much stronger than other commonly available insecticides. Because of this property, the doses needed for mosquito protection are extremely low, generally in the range of 3 to 18 g, making this insecticide highly economical. Deltamethrin is also advantageous because its activity persists over a wide range of temperatures. The low toxicity of this chemical makes it particularly desirable for use as part of a coated garment that is to be worn next to the skin or in close proximity to foodstuffs and the like.

Cypermethrin is yet another synthetic pyrethroid that, along with its emulsifiable concentrate formulations, are non-phytotoxic and have a very low order of dermal toxicity. It is considered to be among the least toxic of the synthetic pyrethroid insecticides. Alpha-cypermethrin is a racemic derivative of cypermethrin that is much more active for insecticidal activity than its parent compound.

As one skilled in the art would appreciate, the formulation of the current invention is not limited to the above-mentioned pyrethroids. Newer synthetic pyrethroids such as cyfluthrin and lambda-cyhalothrin also can be used. Additionally, as one skilled in the art would appreciate, any insecticide which is safe for humans and has the desired level of effectiveness against pests may be used.

Cyclodextrin

The cyclodextrin in the insecticide solution is a non-reducing cyclic oligosaccharide having at least six anhydroglucose units linked in a ring by α-1.4. bonds. Cyclodextrins are produced by the action of the enzyme cyclodextrin glucosyltransferase on starch. The most common cyclodextrins are α-, β-, and γ-cyclodextrins having six (α-), seven (β-), or eight (γ-) anhydroglucose units in the ring structure. Therefore, the preferred cyclodextrins for use in the insecticide solution described herein are α-cyclodextrin, β-cyclodextrin and γ-cyclodextrin or combinations thereof. Because of its high degree of water solubility, which is important to the ease of preparation and the effectiveness of the final product, a hydroxypropyl cyclodextrin is more preferred. The most preferred cyclodextrin is hydroxypropyl β-cyclodextrin. All the hydroxyl groups in cyclodextrins are oriented to the outside of the ring while the glucosidic oxygen and two rings of the non-exchangeable hydrogen atoms are directed towards the interior of the cavity. This combination gives cyclodextrins a hydrophobic inner cavity and a hydrophilic exterior. The insecticide of the insecticide solution acts as a "guest molecule," nestling in the center of the hydrophobic interior, thus forming inclusion complexes. These inclusion complexes bind to the fabric and allow the insecticide to remain attached to the fabric through several wash/rinse cycles, thus prolonging the insecticidal effectiveness of the fabric or material.

Polymeric Binding Agent

The preferred polymeric binding agent of the insecticide solution is polyvinyl acetate (PVA). The primary function of the binding agent is to enhance the binding of the cyclodextrin/insecticide inclusion complex to the fabric. The selection of PVA as the preferred binding agent prolongs the insecticidal performance of the fabric, particularly when used as a bed net. Nets produced using the insecticide solution containing PVA remain effective much longer than nets produced using other polymeric emulsions. Thus, PVA was believed to be an optimal substance for use as binder, resulting in a more effective and longer lasting surface level of insecticide.

Impregnation Method

The insecticide solution or emulsion described above is applied to the fabric using methods well known to those skilled in the art, such as, but not limited to, dipping the fabric into the solution one or more times, soaking the fabric in the solution for a specific amount of time, or spraying the solution onto the fabric. One skilled in the art could easily appreciate that the dipping or soaking can occur in a variety of containers or receptacles for a sufficient amount of time to impart insecticidal properties to the fabric. Furthermore, the formulation of the insecticide solution can be used with a variety of aerosol spraying techniques as well as non-aerosol spraying techniques. Such spraying devices may include, but are not limited to, hand held sprayer and sprayer bottles as well as industrial size applicators.

Fabric

The fabric to be impregnated with the insecticide of the insecticide solution described above includes a variety of different fabric and fabric-type materials and can include natural as well as synthetic fibers or threads. In a preferred embodiment, the fabric is a loosely-woven netting material. This type of fabric is particularly useful as a bednet, which is a net arranged in a loose tent-like configuration, most preferably over a sleeping person, to prevent insect bites during the night. The preferred netting is composed of a variety of materials including, but not limited to, polyester, polypropylene, and polyester or polypropylene derivatives. The fabric can also be woven or sewn into a variety of different materials, including an article of clothing and a tent for outdoor covering such as a tarp or enclosure. The article of clothing can also include military battle dress clothing and material. The fabric can be also woven into a material that is disposable. Furthermore, the fabric can be adapted to form the outer covering of furniture or the like.

One particularly preferred embodiment of the insecticide-impregnated fabric that is particularly useful in an area where mosquito infestation is endemic is outer clothing made of bednet type material that can be worn over conventional clothing. This outer clothing would provide protection from mosquitoes during the day for persons engaged in activities such as walking, hiking, farming and the like.

It should also be appreciated that the fabric can be constructed into a hood or hat material to cover the head, neck and face area. This type of fabric is useful for protecting these highly vulnerable areas of the body.

The present invention is further illustrated by the following non-limiting examples, which are not to be construed in any way as imposing limitations upon the scope thereof. On the contrary, it is to be clearly understood that resort may be had to various other embodiments, modifications. and equivalents thereof which, after reading the description herein, may suggest themselves to those skilled in the art without departing from the spirit of the present invention or the scope of the appended claims.

EXAMPLES

Example 1

Preparation of Insecticide Impregnated Bednet Samples

Insecticide-impregnated bednet samples were prepared as follows. A 3.2 ml volume of de-ionized water and a calculated volume of a particular insecticide formulation, to achieve a desired target impregnation level for the insecticide, was added to a 30 ml beaker. Four 12.5×15.5 cm pieces of polypropylene or polyester netting were evenly stacked on top of each other, then folded several times. The stack of folded netting pieces was then placed into the beaker containing the prepared impregnation solution, and the stack was kneaded about in the beaker for several minutes. A piece of aluminum foil was placed over the beaker to prevent evaporation, and the beaker was placed upside down for at least 1 hour to facilitate further equilibration. The stack was then removed from the beaker, unfolded, and individual netting samples lain flat, in order from top to bottom, on a piece of aluminum foil for drying. After drying was complete, samples 1 (top) and 4 (bottom) were taken and subjected to gas-chromatographic analysis for insecticide content (see below), and the two values obtained were averaged to provide a good approximation of the dosage level of the two remaining samples of impregnated netting, intended for use in either washing or dose-response (mortality) studies.

Alternatively, single 12.5×15.5 cm pieces of netting were dipped in an excess volume of treatment solution. Then, the excess solution was wrung out and the sample placed on aluminum foil for drying. The deposited insecticide concentration on the netting sample was then estimated by knowing the concentration of insecticide in the treatment solution and the approximate volume of treatment solution retained after wringing out.

Bioassays

Insectary-reared and sugar-fed *Anopheles gambiae* mosquitoes (Kisumu [KIS], G3 and Asembo [AB] strains), 3–4 days old, were tested for susceptibility (or resistance) to permethrin-impregnated nets, using the WHO adult mosquito susceptibility test kit. About 20 mosquitoes were used in each assay. Cohort mosquitoes were then used to bioassay the pyrethroid-impregnated netting samples using the WHO cone bioassay with a 3 minute exposure time. During an assay, the cone was held on its side, which placed the net sample in a perpendicular or vertical position with respect to the floor, as is the case when testing an actual hanging net. In each assay 7–12 mosquitoes were used with 3–4 such assays run for each experiment. After exposure for the prescribed time, mortality was determined after the mosquitoes were held overnight (24 hours) in clean cartons with sugar water for nourishment. Final mortality was corrected for control mortality. Knock-down was defined as the number of mosquitoes alive or dead, present on the floor of the carton 30 minutes after exposure. Knock-down is considered to be a more accurate measurement of insecticide efficacy because in the wild any mosquito that falls to the ground serves almost immediately as food for other insects (e.g., ants). Temperature and humidity conducive to the survival of the mosquitoes were maintained.

Gas-Chromatographic Analysis of Insecticide-Impregnated Netting Samples

The concentration of insecticide impregnated onto the netting was determined as follows. The samples of impregnated netting were placed into 20 ml scintillation vials, and 100 $\mu$l of the appropriate internal standard solution (IS) was added, followed by 20 ml of acetone. The samples were shaken on a mechanical shaker for 30 minutes. For each sample, 100 $\mu$l of the acetone extract was transferred to an auto sampler vial followed by 0.9 ml of acetone. After capping, 1 $\mu$l of each sample solution was automatically injected into the gas-chromatographic (GC) system to determine insecticide content. The GC system conditions included a 30 m×530 $\mu$m fused silica capillary column (DB-17), 1 $\mu$m film thickness (J & W Scientific. Folsom, Calif.); carrier flow (nitrogen)=12 ml/min; column temperature=200° C. for 5 minutes, 30° C./min to 280° C.; detection=electron capture; detector temperature=310° C.; and injector temperature=270° C.

Washing

Netting samples were repeatedly washed and each wash and rinse solution was analyzed to determine the concentration of impregnated insecticide removed during each wash cycle. After several wash/rinse cycles, when the insecticidal efficacy had become depleted, the residual insecticide on the net was also determined.

A volume of 100 ml of a standardized detergent (2% aqueous sodium dodecyl sulfate [SDS]) was added to a 4 ounce wide mouth screw-cap bottle. An impregnated net sample (bioassayed beforehand) was folded twice and placed into the SDS solution, and the cap was applied and the bottle was shaken for 5 minutes on a mechanical shaker. After removing the cap, the net sample was removed, wrung out and placed in a 4 ounce bottle containing 100 ml of de-ionized water and shaken for five minutes, after which, the sample was removed, wrung out and left to dry overnight. The sample was rebioassayed the next day and at later times. To each wash solution was added a volume of 100 µl of the appropriate internal standard (IS) solution in acetone, and the contents were vigorously shaken by hand. To the rinse solution was added a 0.5 g quantity of dry SDS, and the contents were shaken to dissolve the SDS. Then a 100 µl volume of IS was added, and the contents were vigorously shaken. Two ml of each wash and rinse solution was then transferred to a 4 ml screw-cap vial, 3 ml of ethyl acetate were added and the contents were shaken. After centrifugation to clarify the ethyl acetate layer, about 1 ml of the ethyl acetate layer of each extract was transferred to an autosampler vial and injected onto the GC system described above to determine insecticide content.

For washing experiments involving permethrin, the wash and rinse solutions were injected directly onto a reversed-phase, high-performance liquid chromatographic system with ultraviolet (UV) detection, to determine the permethrin content of the solutions.

Results

Figure 2:
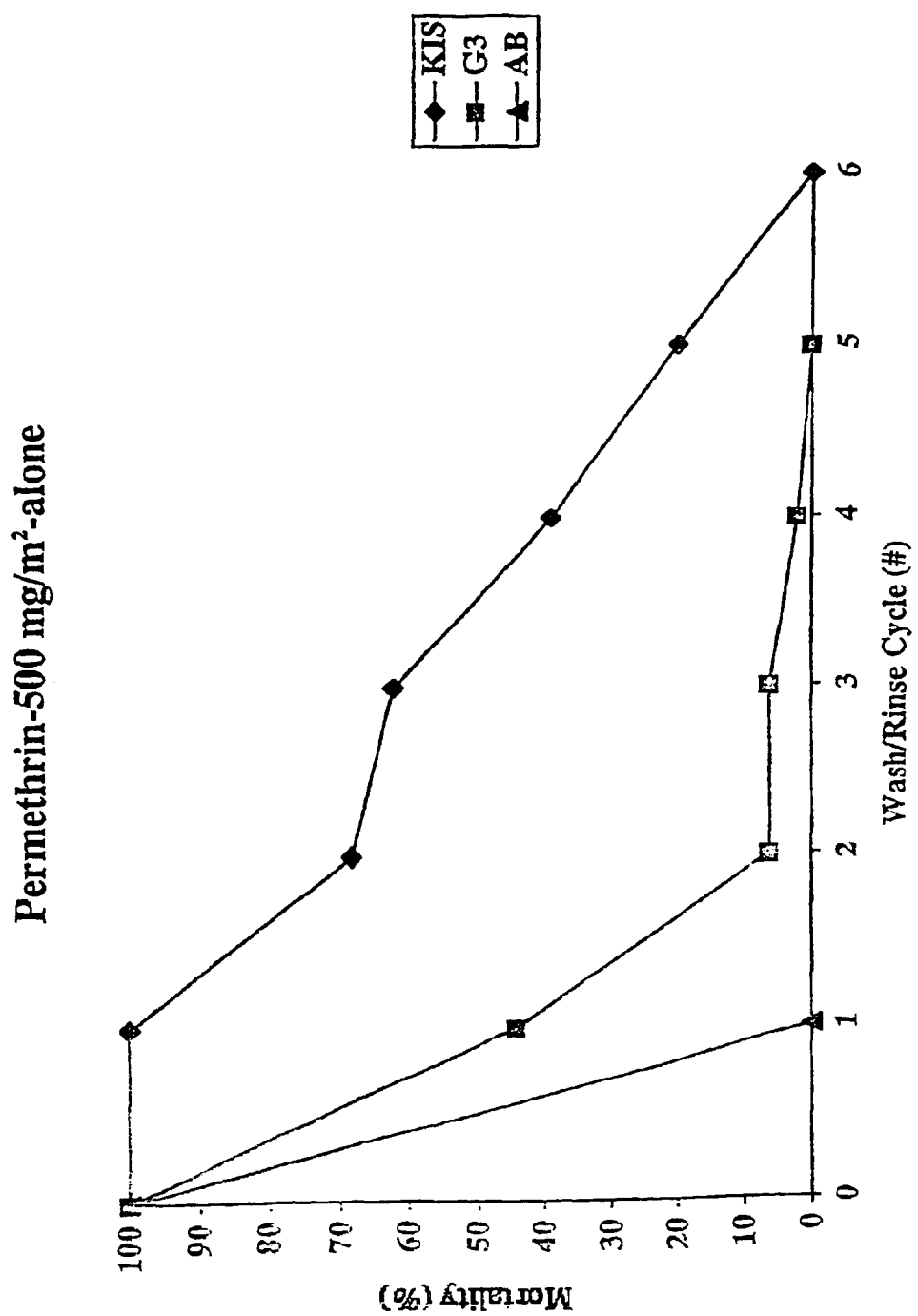
FIG. 2 is a graph showing the effect of wash/rinse cycles on mosquito mortality after exposure of three strains of *A. gambiae* (KIS, diamonds; G3, squares; AB, triangles) to polypropylene bednet samples coated with permethrin alone (500 mg/m$^2$).

In bednets treated with permethrin alone, there was a dramatic decrease in the effectiveness of the bednet within one to five wash/rinse cycles as measured by knock-down and mortality. Nets treated with 500 mg/m$^2$ of permethrin alone were completely ineffective against the AB strain of mosquitoes after just one wash rinse cycle (FIGS. 1, 2). By two wash/rinse cycles, knock-down and mortality had decreased to approximately 20 and 10%, respectively, for the G3 strain. After five wash/rinse cycles, there was less than 50% knock-down and only approximately 20% mortality in KIS mosquitoes exposed to nets treated with 500 mg/m$^2$ of permethrin alone. By six wash/rinse cycles all effectiveness against all strains had completely disappeared.

Figure 3:
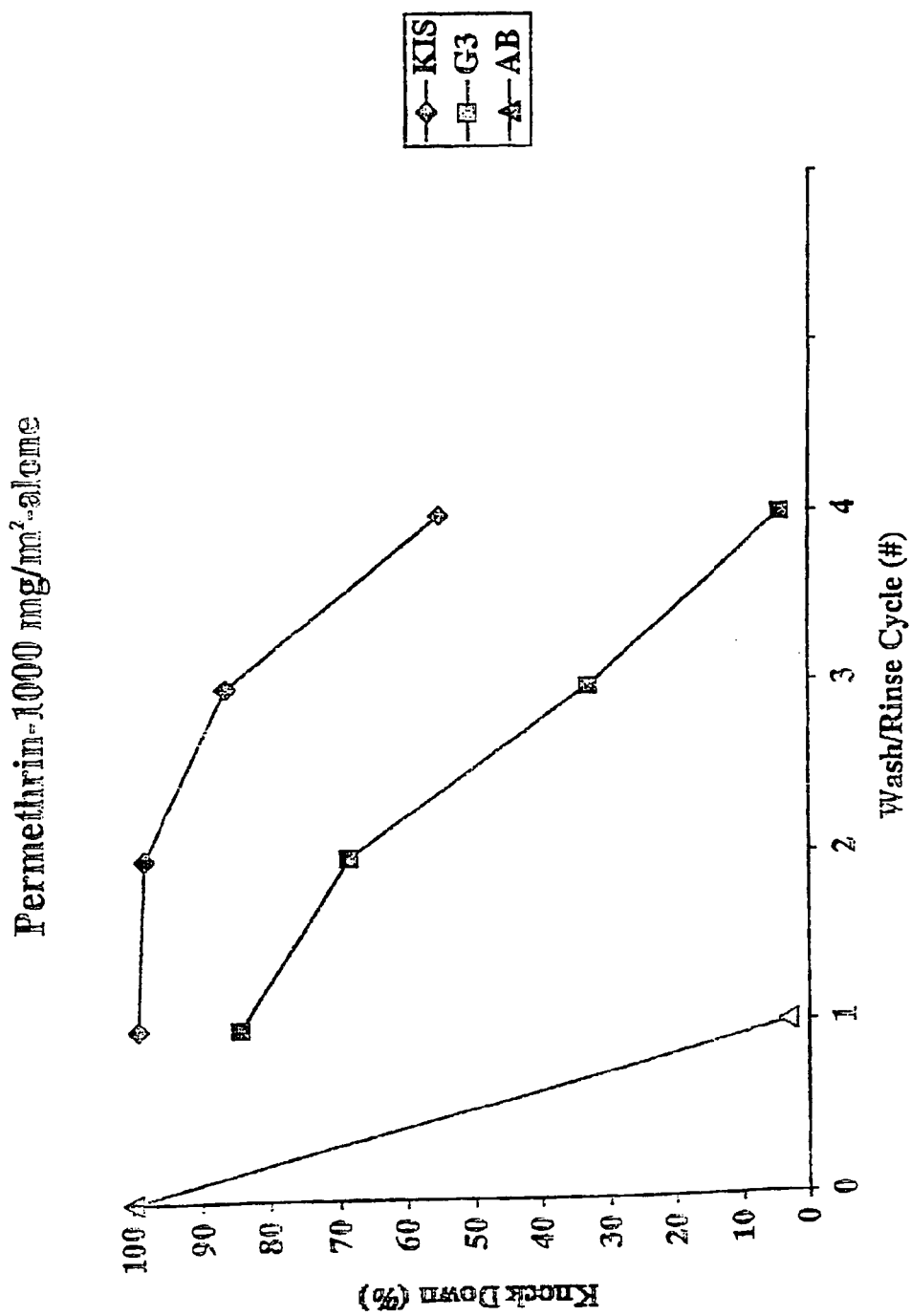
FIG. 3 is a graph showing the effect of wash/rinse cycles on mosquito knock-down after exposure of three strains of *A. gambiae* (KIS, diamonds; G3, squares; AB, triangles) to polypropylene bednet samples coated with permethrin alone (1000 mg/m$^2$).
Figure 4:
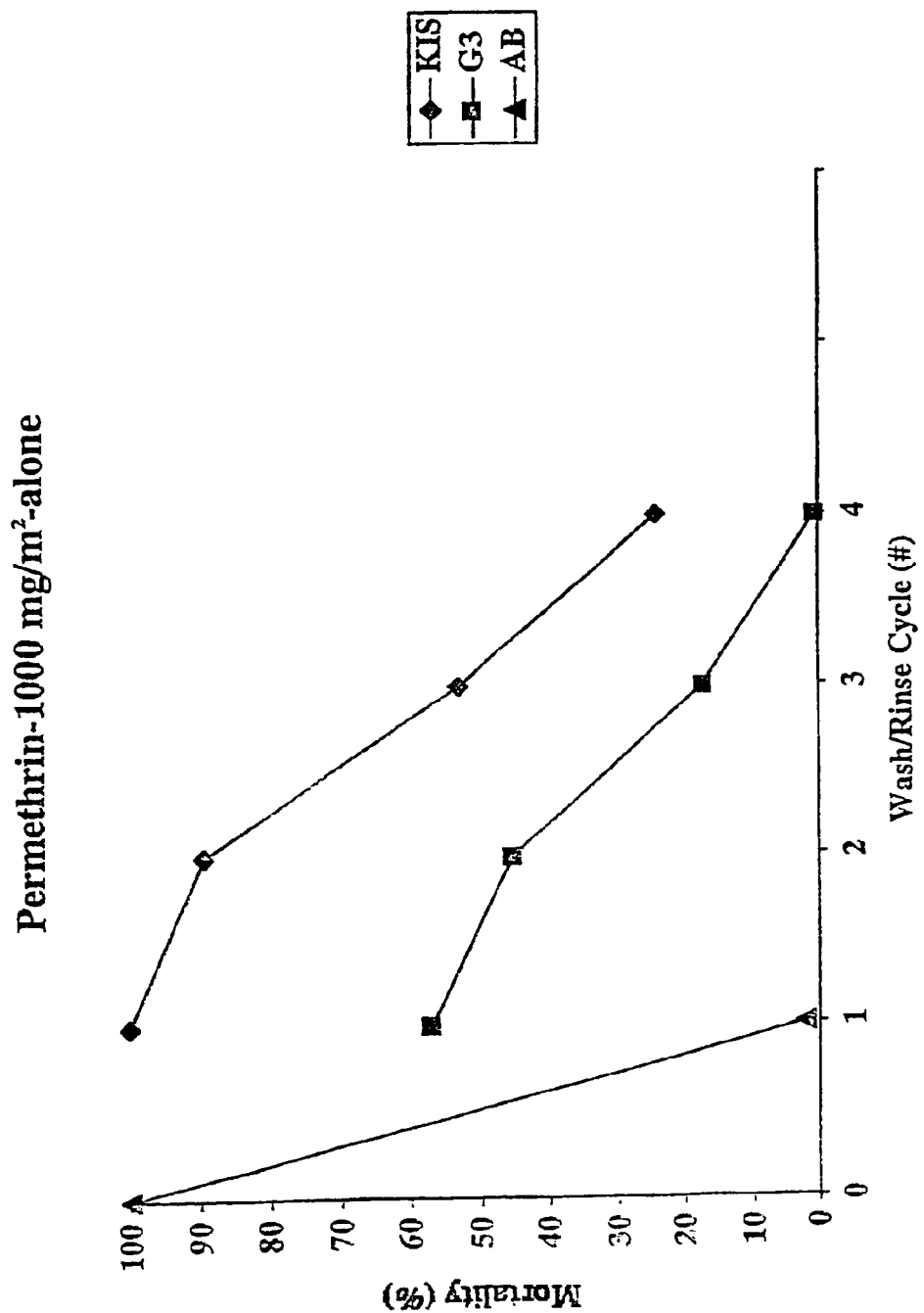
FIG. 4 is a graph showing the effect of wash/rinse cycles on mosquito mortality after exposure of three strains of *A. gambiae* (KIS, diamonds; G3, squares; AB, triangles) to polypropylene bednet samples coated with permethrin alone (1000 mg/m$^2$).

Similarly, nets treated with 1000 mg/m$^2$ permethrin alone, lost most of their effectiveness against all the strains of mosquitoes after four washings (FIGS. 3, 4). When bednets were treated with permethrin alone, most (63–90%) of the insecticide was lost after the first washing (Table 1A, B). This makes bednets prepared by treatment with insecticide alone highly impractical and ineffective.

TABLE 1

Post Wash/Rinse Cycle Concentration Of Permethrin In Bednets Treated With Either 500 Or 1000 mg/m$^2$ Of Permethrin Alone

|  | Wash Cycle # | Amt washed off during a W/R cycle | | Amt (%) washed off during a W/R cycle |
|---|---|---|---|---|
|  |  | mg | mg/m$^2$ | cycle |
| A | W/R = 0 | — | — | — |
| 500 mg/m$^2$ | W/R = 1 | 1.33 | 68.64 | 63.0 |
|  | W/R = 2 | 0.09 | 4.65 | 4.3 |
|  | W/R = 3 | 0.10 | 5.16 | 4.7 |
|  | W/R = 4 | 0.37 | 19.10 | 17.5 |
|  | W/R = 5 | 0.16 | 8.26 | 7.6 |
|  | W/R = 6 | 0.06 | 3.10 | 2.8 |
| B | W/R = 0 | — | — | — |
| 1000 mg/m$^2$ | W/R = 1 | 8.43 | 435.07 | 90.7 |
|  | W/R = 2 | 0.22 | 11.35 | 2.4 |
|  | W/R = 3 | 0.08 | 4.13 | 0.9 |
|  | W/R = 4 | 0.08 | 4.13 | 0.9 |

Example 2

Bednets Treated With Permethrin, Cyclodextrin and PVA

Wash-durable impregnated bednet samples are prepared as follows. A permethrin net impregnation solution or emulsion or suspension is prepared by adding permethrin, PVA, and cyclodextrin to a quantity of water calculated to result in a predetermined permethrin concentration for a single dipping cycle. Usually, a weighed quantity of hydroxypropyl β-cyclodextrin (or other appreciably water-soluble cyclodextrin) is first dissolved into a volume of water. A specific volume of permethrin emulsifiable concentrate formulation to give the desired impregnation concentration, is slowly added to the aqueous cyclodextrin solution with stirring. After further stirring for 1–2 hours to allow inclusion of the insecticide into the cyclodextrin, a commercial PVA emulsion is added with stirring, usually at the rate of 1 drop per ml of resulting impregnation/treatment solution. A 12.5×15.5 cm piece of 100 denier, polyester or polypropylene netting is folded several times and dipped into the suspension. Excess solution is removed by pressing the folded net piece against the sides of the container holding the impregnation suspension. The netting is unfolded and placed flat upon a piece of aluminum foil for a few hours to allow drying, thus forming a polymer layer on the net containing the permethrin/cyclodextrin inclusion complex. For a particular experiment, this dipping process may be repeated 1–2 more times.

Polypropylene bednet samples were prepared as described above at permethrin target concentrations of 250, 500 or 1000 mg/m$^2$ in combination with cyclodextrin (at target concentrations of 1250, 2500 or 5000 mg/m$^2$, respectively) and PVA (at target concentrations of 300, 600 or 1200 mg/m$^2$, respectively). The net samples were tested as described above in Example 1.

Results

Figure 5:
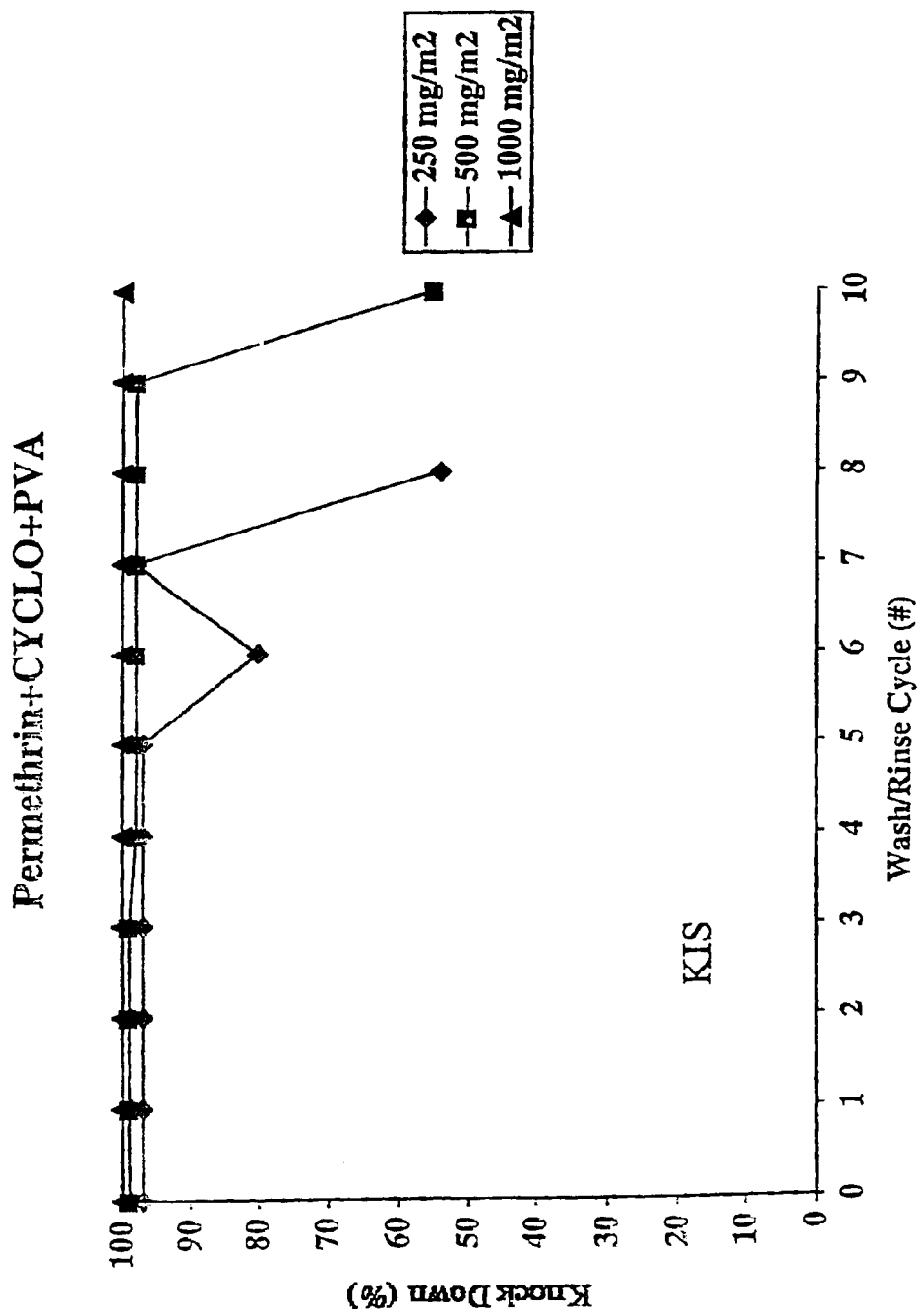
FIG. 5 is a graph shoving the effect of wash/rinse cycles on mosquito knock-down after exposure of *A. gambiae* (KIS) to polypropylene bednet samples coated with permethrin (250 mg/m$^2$, diamonds; 500 mg/m$^2$, squares; 1000 mg/m$^2$, triangles) in combination with PVA (300, 600, and 1200 mg/m$^2$, respectively) and cyclodextrin (1250, 2500, and 5000 mg/m$^2$, respectively).
Figure 6:
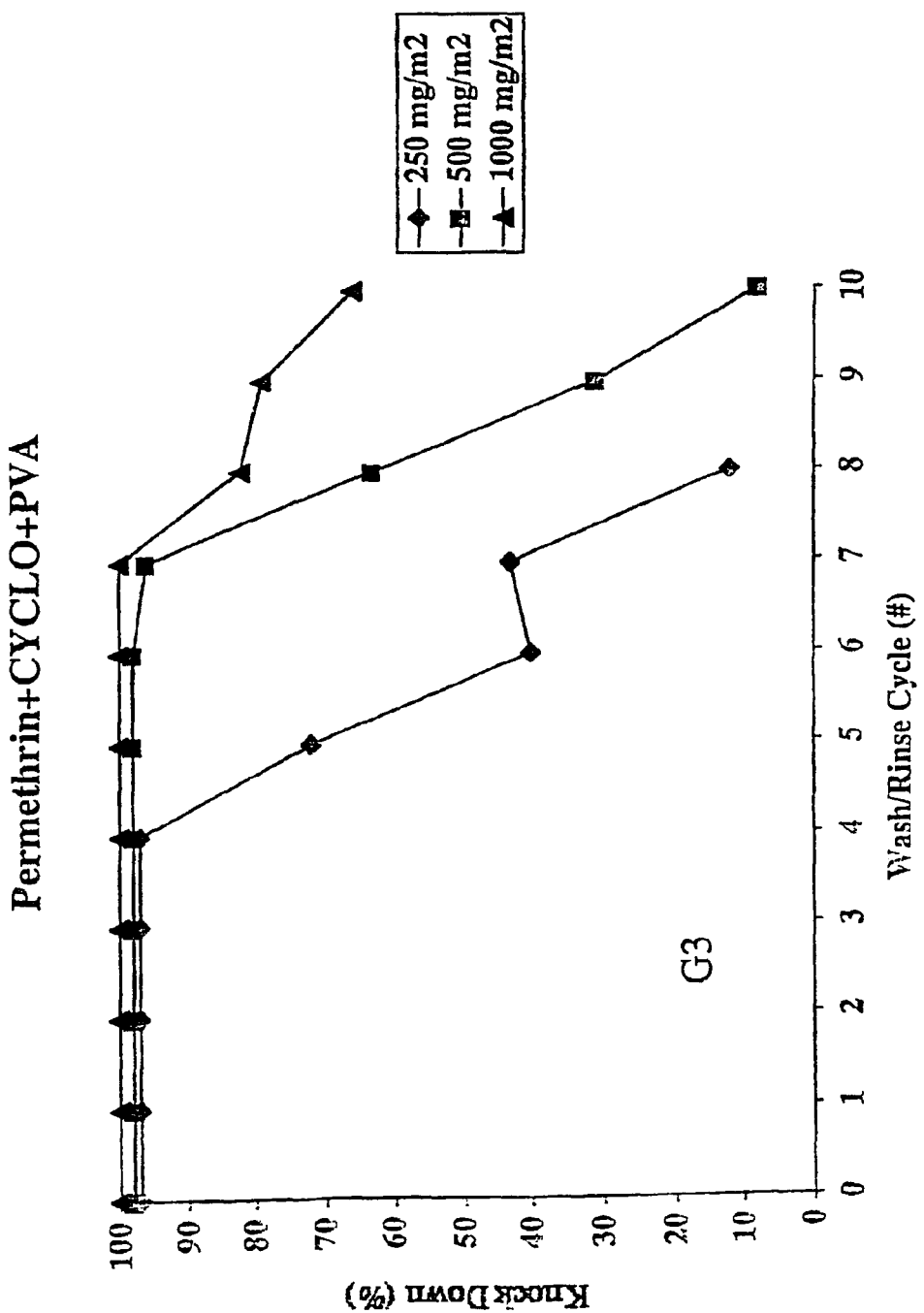
FIG. 6 is a graph showing the effect of wash/rinse cycles on mosquito knock-down after exposure of *A. gambiae* (G3) to polypropylene bednet samples coated with permethrin (250 mg/m$^2$, diamonds; 500 mg/m$^2$, squares; 1000 mg/m$^2$, triangles) in combination with PVA (300, 600, and 1200 mg/$^2$, respectively) and cyclodextrin (1250, 2500, and 5000 mg/m$^2$, respectively).
Figure 7:
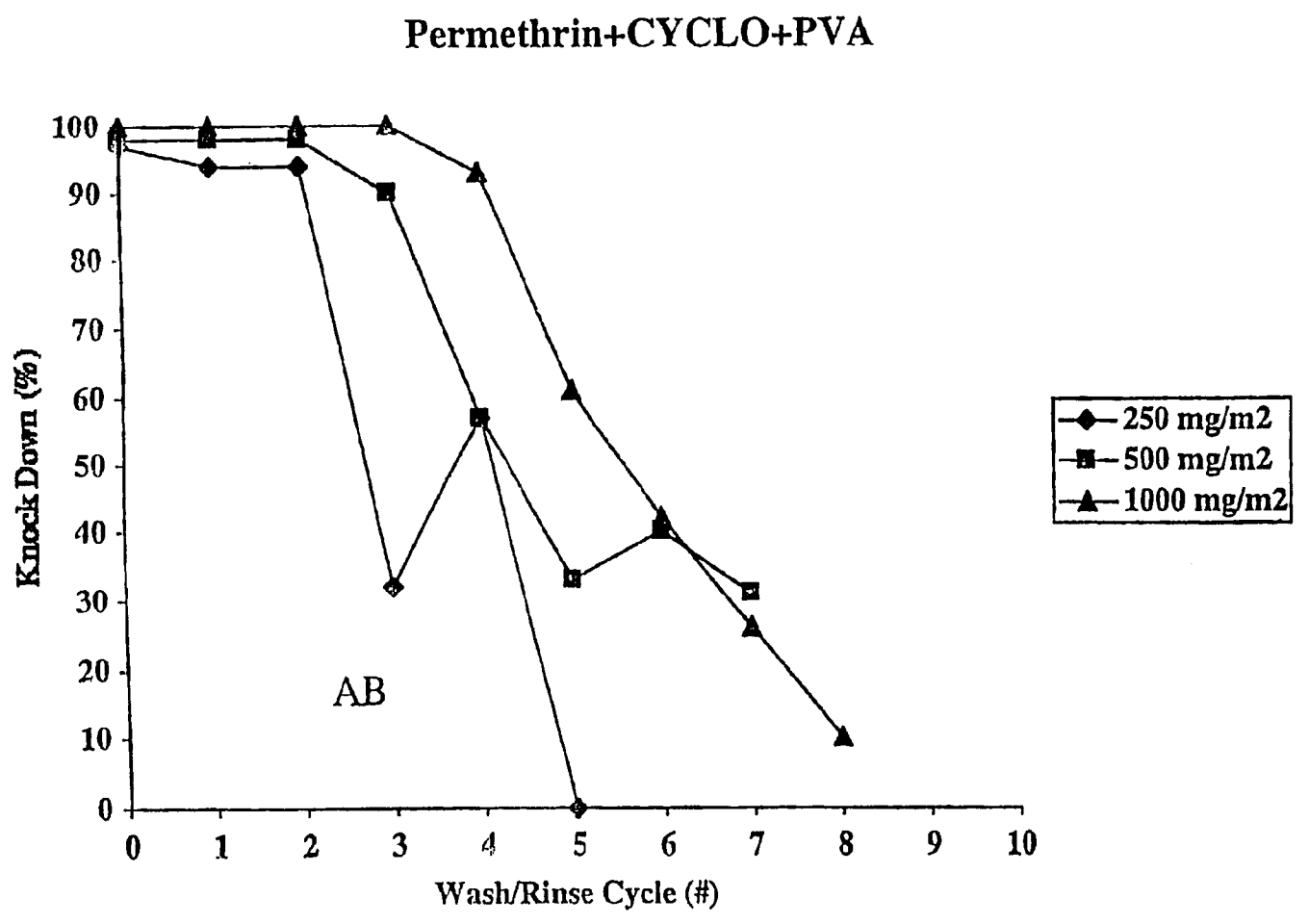

The polypropylene bednet samples impregnated with the treatment solution containing permethrin, cyclodextrin, and PVA, as described, were significantly more effective against all strains of mosquitoes than bednets treated with permethrin alone. Bednets treated with permethrin in concentrations of 250 to 1000 mg/m$^2$ after ten wash/rinse cycles were still 60 to 100% effective in knock-downs against the KIS strain (FIG. 5). Similarly, after ten wash cycles nets treated with the permethrin, cyclodextrin, and PVA formulation maintained almost 80% of their knock-down effectiveness against the G3 strain (FIG. 6). In the AB strain of Anopheles, one known for its resistance to permethrin, bednets maintained over 60% of their knockdown effectiveness after five washings (FIG. 7). This is in sharp contrast to those treated with permethrin alone (FIGS. 3, 4).

Figure 8:
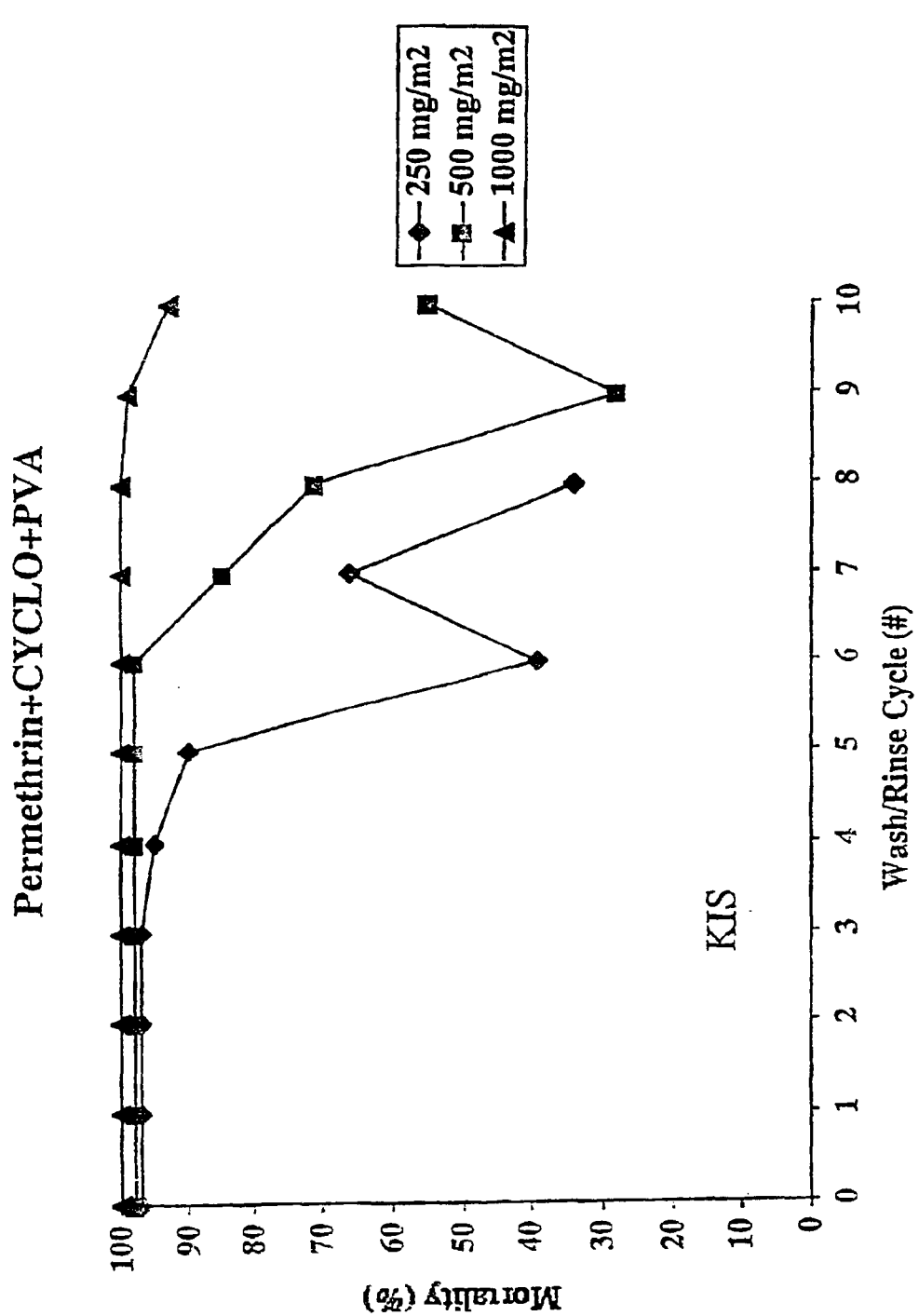
FIG. 8 is a graph showing the effect of wash/rinse cycles on mosquito mortality after exposure of *A. gambiae* (KIS) to polypropylene bednet samples coated with permethrin (250 mg/m$^2$, diamonds; 500 mg/m$^2$, squares; 1000 mg/m$^2$, triangles) in combination with PVA (300, 600, and 1200 mg/m$^2$, respectively) and cyclodextrin (1250, 2500, and 5000 mg/m$^2$, respectively).
Figure 9:
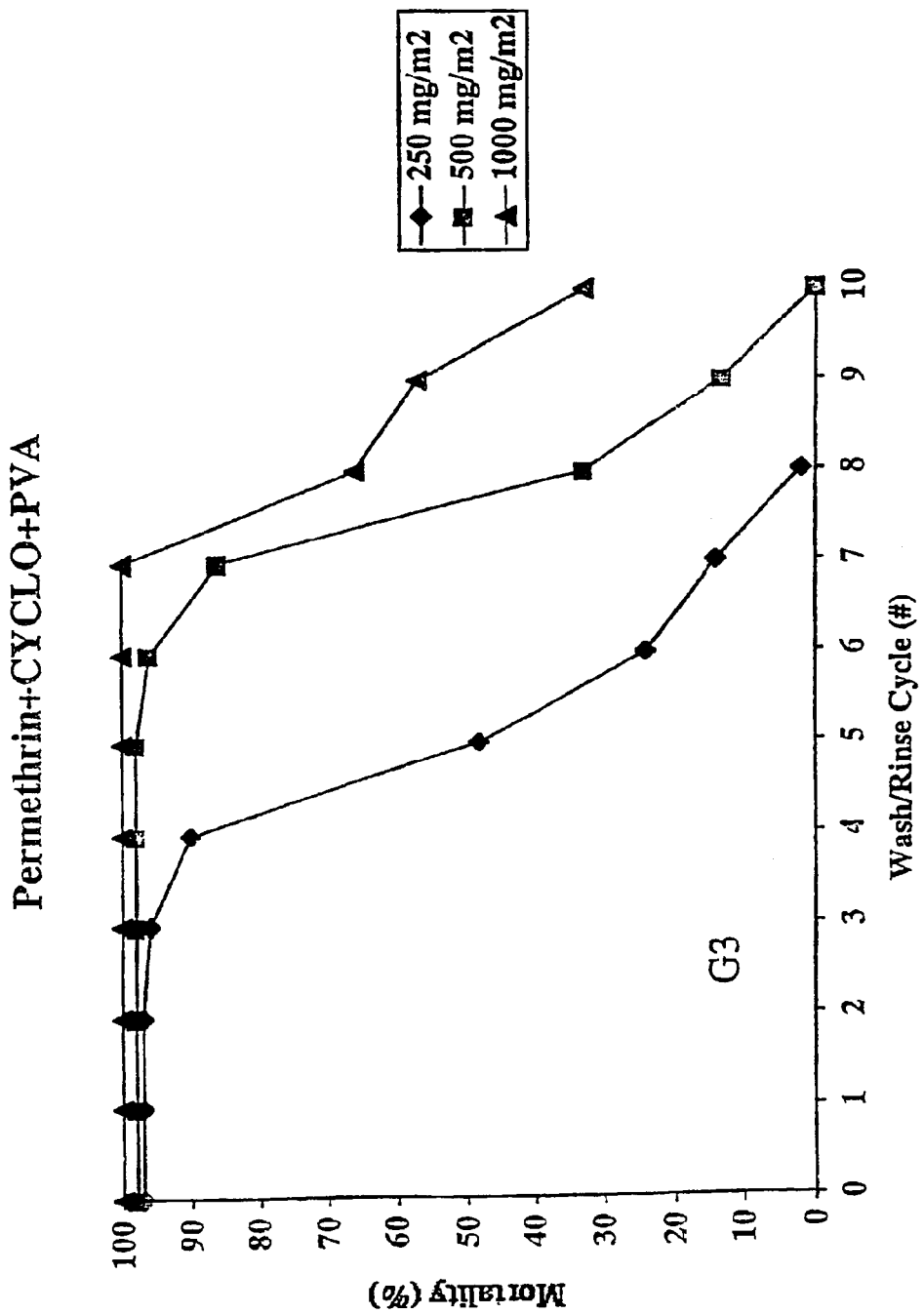
FIG. 9 is a graph showing the effect of wash/rinse cycles on mosquito mortality after exposure of *A. gambiae* (G3) to polypropylene bednet samples coated with permethrin (250 mg/m$^2$, diamonds; 500 mg/m$^2$, squares; 1000 mg/m$^2$, triangles) in combination with PVA (300, 600, and 1200 mg/m$^2$, respectively) and cyclodextrin (1250, 2500, and 5000 mg/m$^2$, respectively).
Figure 10:
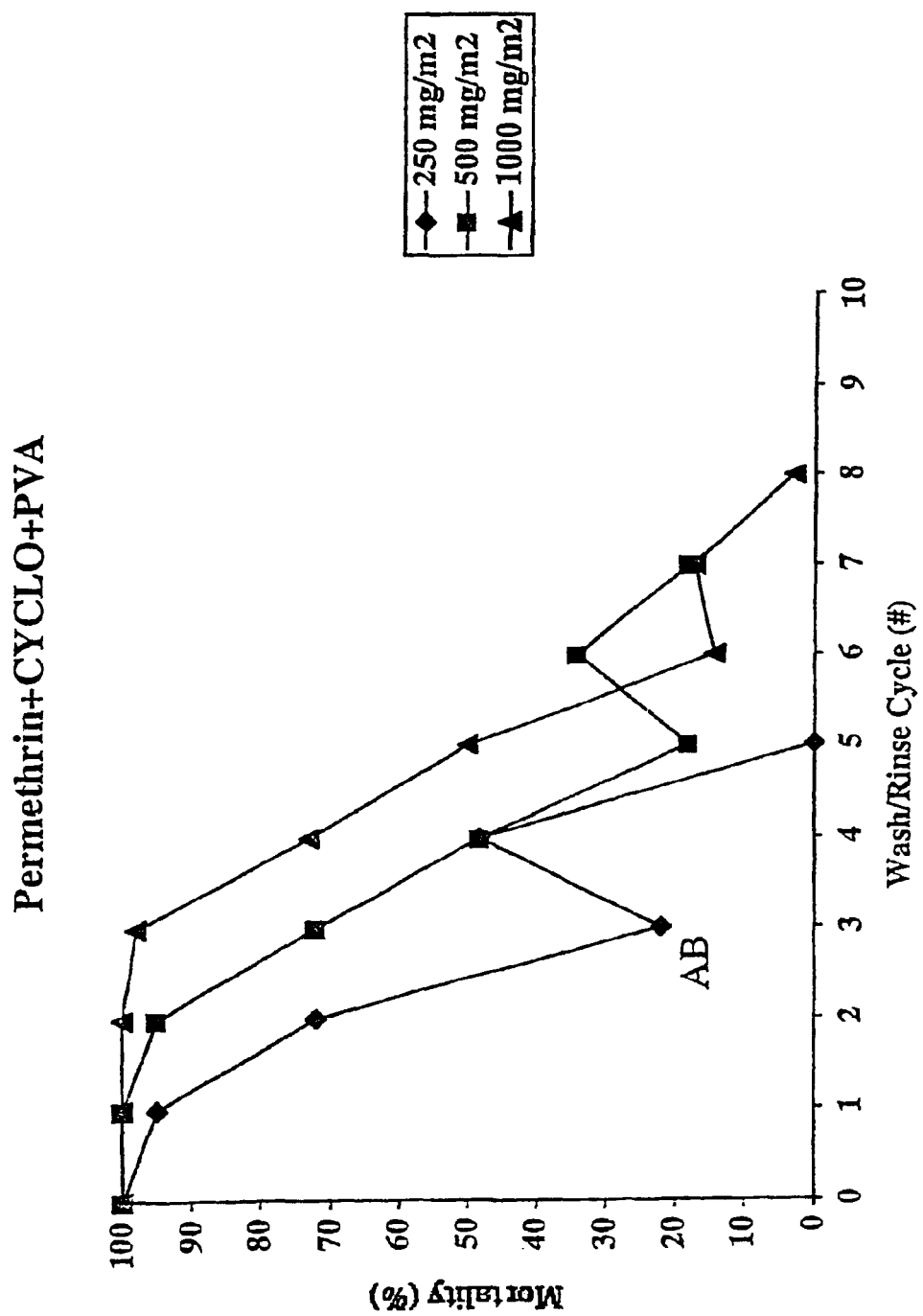
FIG. 10 is a graph showing the effect of wash/rinse cycles on mosquito mortality after exposure of *A. gambiae* (AB) to polypropylene bednet samples coated with permethrin (250 mg/m$^2$, diamonds; 500 mg/m$^2$, squares; 1000 mg/m$^2$, triangles) in combination with PVA (300, 600, and 1200 mg/m$^2$, respectively) and cyclodextrin (1250, 2500, and 5000 mg/m$^2$, respectively).
Figure 11:
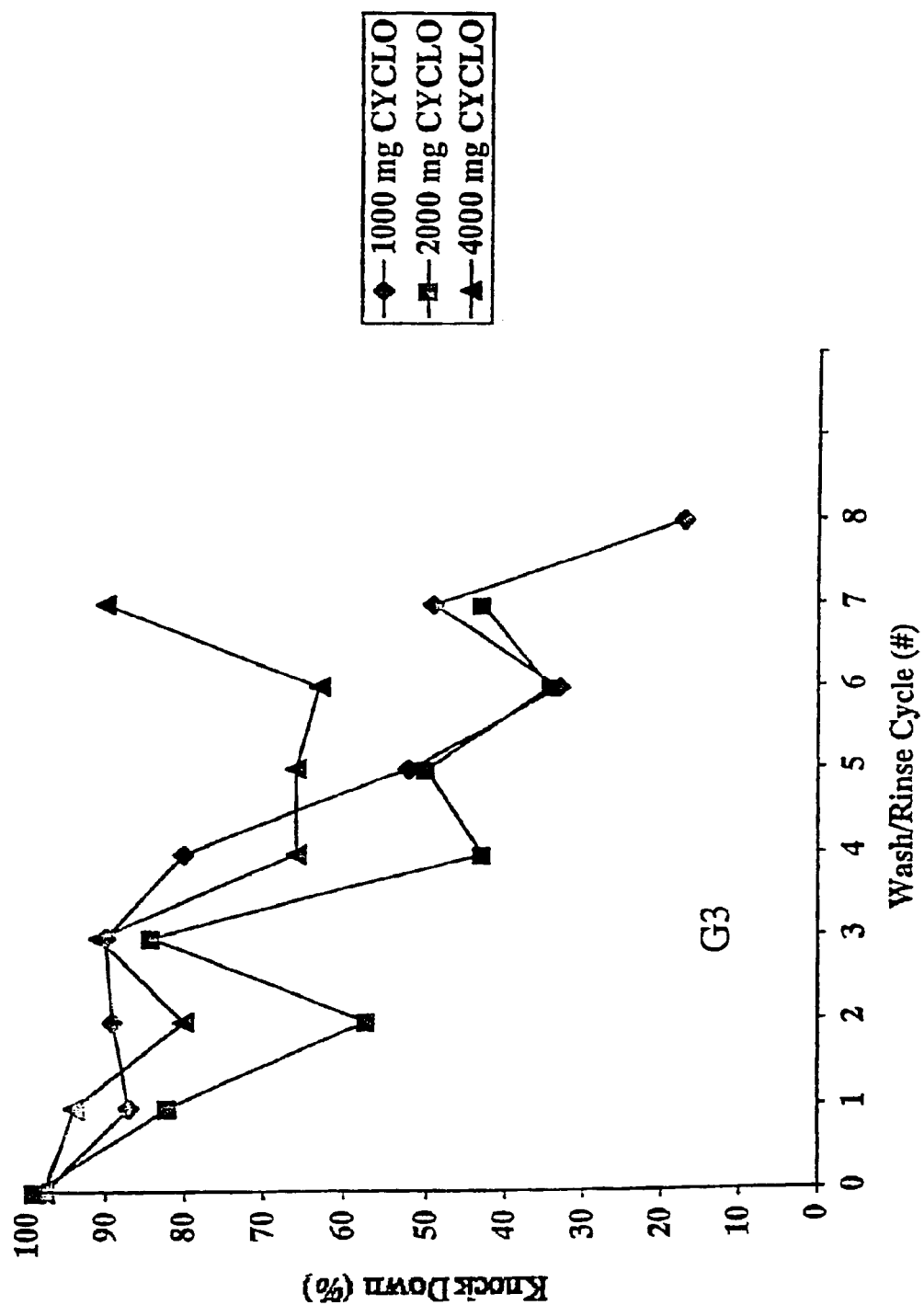
FIG. 11 is a graph showing the effect of wash/rinse cycles on mosquito knock-down after exposure of *A. gambiae* (G3) to polyester bednet samples coated with permethrin and PVA at target concentrations of 3000 mg/m$^2$ and varying target concentrations of cyclodextrin of 3000 (diamonds), 6000 (squares), and 12000 (triangles) mg/m$^2$, respectively.
Figure 12:
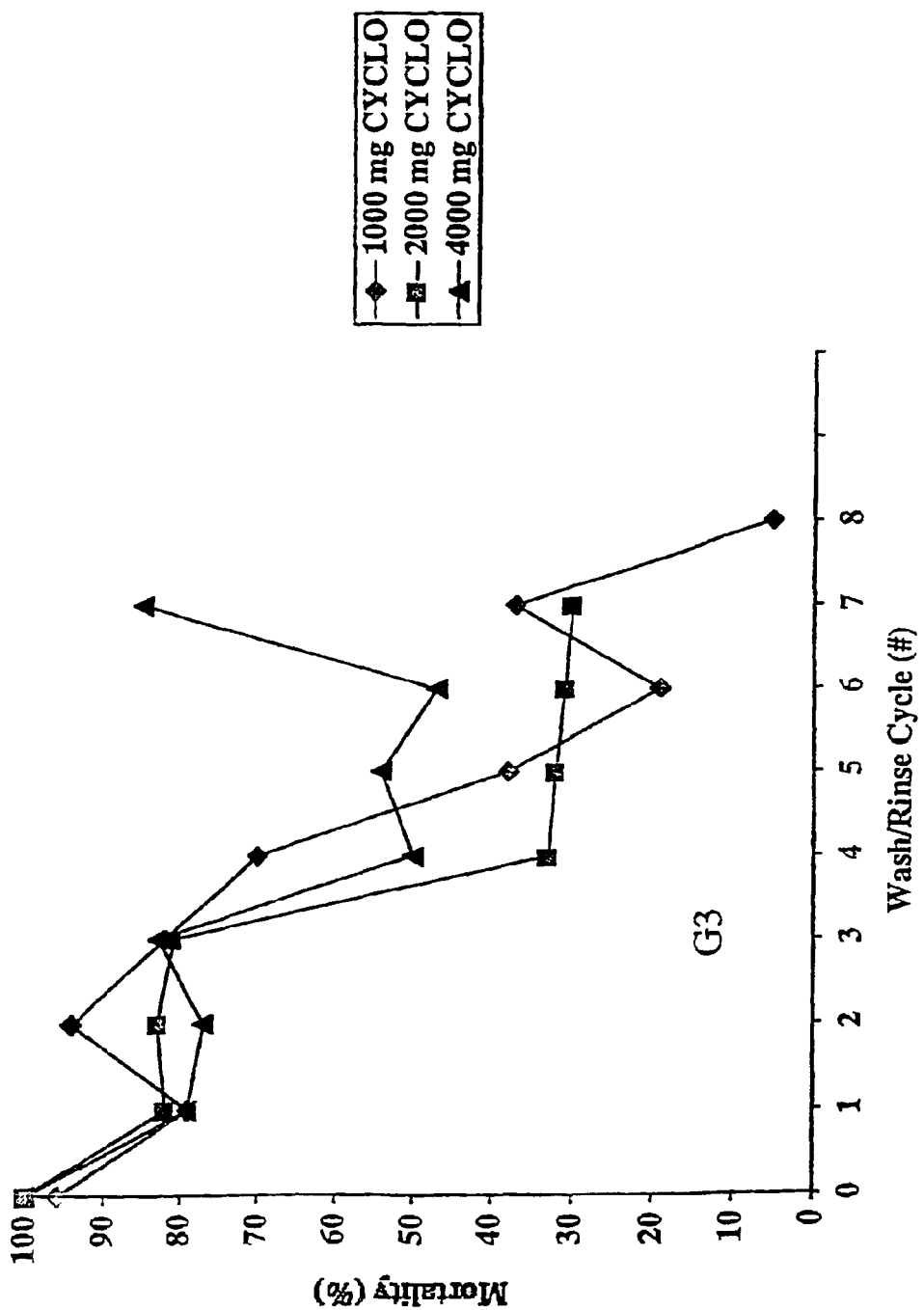
FIG. 12 is a graph showing the effect of wash/rinse cycles on mosquito mortality after exposure of *A. gambiae* (G3) to polyester bednet samples coated with permethrin and PVA at target concentrations of 3000 mg/m$^2$ and varying target concentrations of cyclodextrin of 3000 (diamonds), 6000 (squares), and 12000 (triangles) mg/m$^2$, respectively.

Bednets treated with the permethrin, cyclodextrin, and PVA formulation also demonstrated significant mortality for a greater number of wash cycles. Mortality was maintained after ten wash/rinse cycles in the KIS strain (FIG. 8). Over 60% mortality was maintained in bednets treated with 1000 mg/m$^2$ of permethrin, cyclodextrin, and PVA after eight wash cycles in the G3 strain of mosquitoes (FIG. 9). FIG. 10 shows that even in the fairly resistant AB strain, over 70% mortality is maintained after four wash/rinse cycles. This was significantly greater than in bednets treated with permethrin alone (FIG. 1) in which all effectiveness with this strain was lost after one wash/rinse cycle.

The effectiveness of the permethrin, cyclodextrin. and PVA formulation can be further appreciated by the results in Table 2, below, which demonstrate that relatively little permethrin is washed off per wash cycle compared to nets treated with permethrin alone (Table 1). Thus, the formulation allows more insecticide to remain on the net following repeated wash/rinse cycles. The superior results on mortality and knock-down in bednets treated with the formulation described herein show its superiority over methods currently used in fighting disease carrying mosquitoes.

TABLE 2

Post Wash/Rinse Cycle Concentration Of Permethrin In Bednets Treated With 250, 500 Or 1000 mg/m$^2$ Of Permethrin, Cyclodextrin and PVA

| | Wash Cycle # | Amt washed off during a W/R cycle mg | Amt washed off during a W/R cycle mg/m$^2$ | Amt (%) washed off during a W/R cycle |
|---|---|---|---|---|
| A 250 mg/m$^2$ | W/R = 0 | — | — | — |
| | W/R = 1 | 0.55 | 28.38 | 19.4 |
| | W/R = 2 | 0.25 | 12.90 | 8.8 |
| | W/R = 3 | 0.31 | 16.00 | 10.9 |
| | W/R = 4 | 0.18 | 9.29 | 6.3 |
| | W/R = 5 | 0.37 | 19.10 | 13.0 |
| | W/R = 6 | 0.25 | 12.89 | 8.8 |
| | W/R = 7 | 0.19 | 9.81 | 6.7 |
| | W/R = 8 | 0.09 | 4.64 | 3.2 |
| B 500 mg/m$^2$ | W/R = 0 | — | — | — |
| | W/R = 1 | 0.82 | 42.32 | 15.1 |
| | W/R = 2 | 0.39 | 20.13 | 7.2 |
| | W/R = 3 | 0.37 | 19.10 | 6.8 |
| | W/R = 4 | 0.24 | 12.38 | 4.4 |
| | W/R = 5 | 0.67 | 34.58 | 12.3 |
| | W/R = 6 | 0.45 | 23.22 | 8.3 |
| | W/R = 7 | 0.40 | 20.64 | 7.4 |
| | W/R = 8 | 0.26 | 13.42 | 4.8 |
| | W/R = 9 | 0.18 | 9.29 | 3.3 |
| | W/R = 10 | 0.19 | 9.81 | 3.5 |
| C 1000 mg/m$^2$ | W/R = 0 | — | — | — |
| | W/R = 1 | 1.69 | 87.22 | 19.0 |
| | W/R = 2 | 0.84 | 43.35 | 9.5 |
| | W/R = 3 | 0.53 | 27.35 | 6.0 |
| | W/R = 4 | 0.67 | 34.58 | 7.5 |
| | W/R = 5 | 0.45 | 23.22 | 5.1 |
| | W/R = 6 | 0.37 | 19.10 | 4.2 |
| | W/R = 7 | 0.33 | 17.03 | 3.7 |
| | W/R = 8 | 0.45 | 23.22 | 5.1 |
| | W/R = 9 | 0.45 | 23.22 | 5.1 |
| | W/R = 10 | 0.27 | 13.94 | 3.0 |
| | W/R = 11 | 0.44 | 22.71 | 5.0 |

Example 3

Comparison of Various Concentrations of Cyclodextrin

Polyester bednet samples were prepared similarly as indicated in Example 2. Treatment solutions/emulsions were prepared to result in target concentrations of 1000 mg/m$^2$ of permethrin, 1000 mg/m$^2$ of PVA, and varying target concentrations of concentrations of cyclodextrin of 1000, 2000, and 4000 mg/$^2$, respectively, following a single dipping. Samples of netting were dipped three times into each treatment solution/emulsion, where each sample was allowed to dry overnight before being re-dipped. Thus, the resulting theoretical target concentrations (assuming no material loss of material deposited in previous dipping during the re-dipping) were 3000 mg/m$^2$ for permethrin and PVA and 3000, 6000, and 12,000 mg/m$^2$, respectively, for cyclodextrin. The net samples were tested as indicated in Example 1, above.

Results

Figure 13:
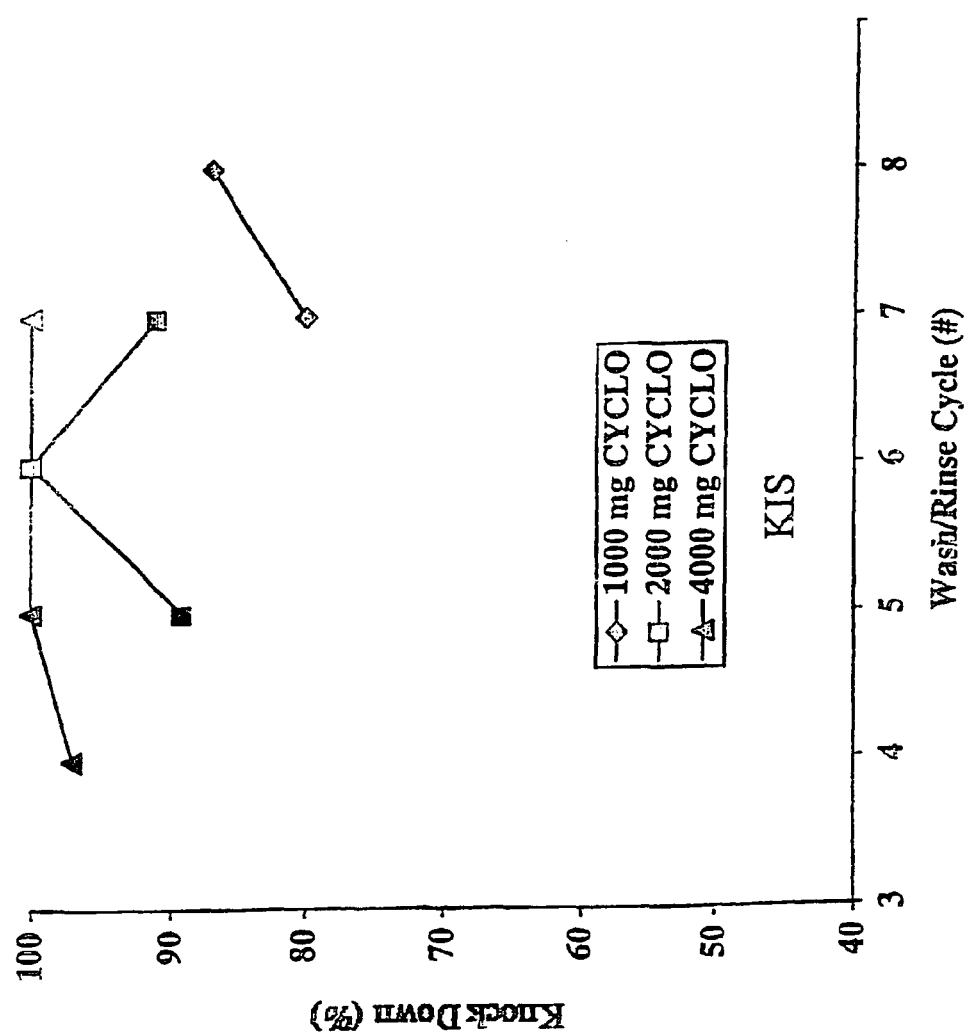
FIG. 13 is a graph showing the effect of wash/rinse cycles on mosquito knock-down after exposure of *A. gambiae* (KIS) to polyester bednet samples coated with permethrin and PVA at target concentrations of 3000 mg/m$^2$ and varying target concentrations of cyclodextrin of 3000 (diamonds), 6000 (squares), and 12000 (triangles) mg/m$^2$, respectively.
Figure 14:
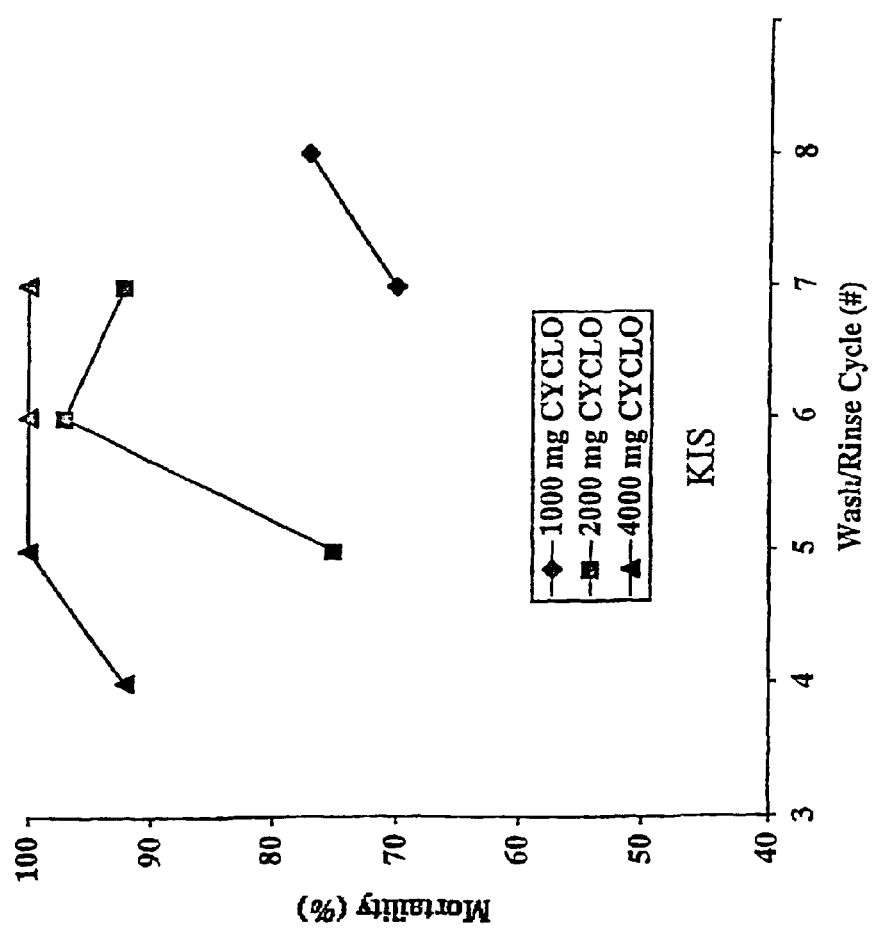
FIG. 14 is a graph showing the effect of wash/rinse cycles on mosquito mortality after exposure of *A. gambiae* (KIS) to polyester bednet samples coated with permethrin and PVA at target concentrations of 3000 mg/m$^2$ and varying target concentrations of cyclodextrin of 3000 (diamonds). 6000 (squares), and 12000 (triangles) mg/m$^2$, respectively.

As seen in FIGS. 11–14, increasing concentrations of cyclodextrin increased the effectiveness of the formulation with respect to both knock-down and mortality. This increased effectiveness can be seen in both the G3 (FIGS. 11, 12) and in the KIS strains (FIGS. 13, 14). Thus, with a greater amount of cyclodextrin added to the formulation of the current invention, there was a greater adherence of insecticide to the bednet over a longer period of time. The increased retention of insecticide on the bednet can be further seen in Table 3, below, which shows that there are only very small amounts of insecticide washed off during each successive wash cycle.

TABLE 3

Post Wash/Rinse Cycle Concentration Of Permethrin In Bednets Treated With Varying Concentrations of Cyclodextrin

| | Wash Cycle # | Amt washed off during a W/R cycle mg | Amt washed off during a W/R cycle mg/m$^2$ | Amt (%) washed off during a W/R cycle |
|---|---|---|---|---|
| A Cyclodextrin 3000 mg/m$^2$ | W/R = 0 | — | — | — |
| | W/R = 1 | 11.83 | 611 | 40.0 |
| | W/R = 2 | 3.07 | 158 | 10.3 |
| | W/R = 3 | 3.64 | 188 | 12.3 |
| | W/R = 4 | 1.24 | 64 | 4.2 |
| | W/R = 5 | 1.30 | 67 | 4.4 |
| | W/R = 6 | 1.51 | 78 | 5.1 |
| | W/R = 7 | 1.05 | 54 | 3.5 |
| | W/R = 8 | 0.88 | 45 | 2.9 |
| B 6000 mg/m$^2$ | W/R = 0 | — | — | — |
| | W/R = 1 | 15.6 | 805 | 42.9 |
| | W/R = 2 | 4.07 | 210 | 11.2 |
| | W/R = 3 | 2.27 | 327 | 17.4 |
| | W/R = 4 | 2.94 | 152 | 8.1 |
| | W/R = 5 | 1.71 | 88 | 4.7 |
| | W/R = 6 | 1.09 | 56 | 3.0 |
| | W/R = 7 | 1.07 | 55 | 2.9 |
| C 12,000 mg/m$^2$ | W/R = 0 | — | — | — |
| | W/R = 1 | 7.21 | 372 | 21.9 |
| | W/R = 2 | 6.67 | 344 | 20.2 |
| | W/R = 3 | 2.51 | 130 | 7.6 |
| | W/R = 4 | 1.86 | 96 | 5.6 |
| | W/R = 5 | 1.21 | 62 | 3.6 |
| | W/R = 6 | 1.53 | 79 | 4.6 |
| | W/R = 7 | 0.98 | 51 | 3.0 |

Comparison of Polypropylene and Polyester Netting

Comparison of the results obtained for Examples 2 and 3 above, indicate that with polypropylene netting. effective, and durable bednets can be produced using much less (at least five-fold in the case of permethrin) insecticide, PVA and cyclodextrin than required for polyester netting. This is attributed to the mono-filament nature of the polypropylene "thread" as opposed to multi-filament nature of the polyester "thread", providing inaccessible (to the mosquito) areas for insecticide, PVA and cyclodextrin to bind. Polypropylene is known for its non-adsorptive properties and is not usually recommended for bednets due to difficulty in impregnating. Thus, with the use of PVA and a cyclodextrin of appreciable water solubility, such as hydroxypropyl beta-cyclodextrin, non-adsorptive materials such as polypropylene can be effectively treated with insecticides to produce bednets (or other fabric items for personal protection) of superior quality in terms of durability to washing and effectiveness in killing mosquitoes.

All of the patents, publications and other references mentioned herein are hereby incorporated by reference.

Modifications and variations of the present methods and compositions will be obvious to those skilled in the art from the foregoing detailed description. Such modifications and variations are intended to come within the scope of the appended claims.

We claim:

1. A method of impregnating a bednet with an insecticide composition produced by contacting the bednet with an insecticide composition comprising an insecticide, a cyclodextrin, and a binding agent resulting in an impregnated bednet.

2. The method of claim 1 wherein the bednet is a polyester bednet.

3. The method of claim 1 wherein the bednet is a polypropylene bednet.

4. The method of claim 1, wherein the insecticide is a pyrethroid.

5. The method of claim 4 wherein the pyrethroid is permethrin, deltamethrin, cyfluthrin, alpha-cypermethrin, etofenprox, lambda-cyhalothrin, or a combination thereof.

6. The method of claim 1, wherein the cyclodextrin is a water-soluble cyclodextrin.

7. The method of claim 1, wherein the cyclodextrin comprises α-cyclodextrin, β-cyclodextrin, γ-cyclodextrin, or a combination thereof.

8. The method of claim 1, wherein the cyclodextrin is a hydroxypropyl derivative of β-cyclodextrin.

9. The method of claim 1, wherein the binding agent is a polymeric binding agent.

10. The method of claim 1, wherein the binding agent is polyvinyl acetate.

11. A method of impregnating a fabric in the form of a net with an insecticide composition produced by contacting the net with the insecticide composition comprising a pyrethroid a cyclodextrin, and a binding agent resulting in an impregnated net.

12. The method of claim 11 wherein the net is a polyester net.

13. The method of claim 11 wherein the net is a polypropylene net.

14. The method of claim 11 wherein the pyrethroid is permethrin, deltamethrin, cyfluthrin, alpha-cypermethrin, etofenprox, lambda-cyhalothrin, or a combination thereof.

15. The method of claim 11 wherein the cyclodextrin is a water-soluble cyclodextrin.

16. The method of claim 11 wherein the cyclodaxtrin comprises α-cyclodextrin, β-cyclodextrin, γ-cyclodextrin, or a combination thereof.

17. The method of claim 11 wherein the cyclodextrin is a hydroxypropyl derivative of β-cyclodextrin.

18. The method of claim 11, wherein the binding agent is a polymeric binding agent.

19. The method of claim 11, wherein the binding agent is polyvinyl acetate.

* * * * *